United States Patent [19]

Kottemann

[11] Patent Number: 4,585,414
[45] Date of Patent: Apr. 29, 1986

[54] ORTHODONTIC ARCH WIRE

[76] Inventor: William J. Kottemann, 755 Tonkawa Rd., Long Lake, Minn. 55356

[21] Appl. No.: 693,381

[22] Filed: Jan. 22, 1985

Related U.S. Application Data

[63] Continuation-in-part of Ser. No. 501,482, Jun. 6, 1983, abandoned.

[51] Int. Cl.⁴ .............................................. A61C 3/00
[52] U.S. Cl. ............................................................ 433/20
[58] Field of Search ........................... 433/20; 528/391

[56] References Cited

U.S. PATENT DOCUMENTS

| Re. 30,332 | 7/1980 | Wallshein | 433/20 |
| Re. 30,593 | 4/1981 | Wallshein | 433/20 |
| 3,504,438 | 4/1970 | Wittman et al. | 433/20 |
| 3,563,961 | 2/1971 | Pickle et al. | 528/391 |
| 3,773,720 | 11/1973 | Vogel | 528/391 |
| 3,988,832 | 11/1976 | Wallshein | 433/21 |
| 4,024,119 | 5/1977 | Sonnenberg | 528/391 |
| 4,050,156 | 9/1977 | Chasanoff et al. | 433/20 |

*Primary Examiner*—John J. Wilson
*Attorney, Agent, or Firm*—Orrin M. Haugen; Thomas J. Nikolai; Lloyd L. Zickert

[57] ABSTRACT

An article of manufacture for use in orthodontic procedures, comprising an extruded plastic rod reinforced with a stainless steel wire core. The article is found to exhibit substantially greater flexibility and resiliency than a stainless steel wire of the same outside diameter.

10 Claims, 3 Drawing Figures

ORTHODONTIC ARCH WIRE

CROSS-REFERENCE TO RELATED APPLICATION

The present application is a continuation-in-part of my copending application Ser. No. 501,482, filed June 6, 1983, entitled "ORTHODONTIC WIRE", now abandoned.

BACKGROUND OF THE INVENTION

I. Field of the Invention

This invention relates generally to orthodontic appliances, and more specifically to a new article of manufacture useful in the correction of maloccluded teeth.

II. Discussion of the Prior Art

In the correction of alignment, positioning and malocclusion of teeth, various mechanical arrangements are used for applying steady forces to the teeth over a prolonged period of time such that the teeth are urged into an aligned disposition within the oral cavity. Typically, bands or brackets are fastened to certain teeth and then a wire arrangement, referred to as an arch wire, is fastened to the bands with the arch serving to apply forces in appropriate directions so as to urge the affected teeth into a different positional orientation. The arch wire is commonly drawn from stainless steel and it is important that it possess properties of flexibility so that it can be bent into a desired shape while, at the same time, exhibiting sufficient stiffness and resiliency (inherent memory property) such that desired forces are imparted upon the teeth to be repositioned.

In the past, orthodontists have primarily employed strands of stainless steel wires having either a circular or square cross-section in fabricating orthodontic arches. While stainless steel wires of a given diameter, i.e., typically in the range of 0.016 to 0.022 inches are commonly employed, they suffer from a lack of flexibility because that outside diameter is necessary to ensure that the wire will have the requisite resiliency to provide the desired forces upon the teeth. While reducing the diameter may render the wire more flexible, its resiliency is correspondingly reduced such that the wire is subject to permanent deformation and/or breakage. More recently, an arch wire formed from a nickel-titanium alloy and sold under the trademark, Nitinol Activ-Arch, by the Unitek Corporation of Monrovia, California, has been introduced which possesses the desirable characteristics of reduced stiffness (greater flexibility) and high resistance to deformation as compared to stainless steel of comparable dimensions. The use of arch wires of Nitinol alloy in orthodontia is described in the Andreason U.S. Pat. No. 4,037,324.

In addition, orthodontic work is frequently performed on patients who may be somewhat self-conscious over their appearance and are, at times, embarrassed by the presence of the orthodontic appliances on their teeth. Stainless steel wires of a requisite diameter tend to be somewhat unsightly. The Chasanoff U.S. Pat. No. 4,050,156 suggests coating a stainless arch wire with a plastic matrix in which a suitable colorant is intermixed so as to match the natural tooth color of the patient. Here, however, the plastic material is not used as a structural member as in the present invention, but is only used as a method of applying a colorant to a stainless steel surface.

SUMMARY OF THE INVENTION

In accordance with the present invention, there is provided a dental arch wire comprising an extruded, flexible plastic rod of polysulfone or Ultem reinforced with a stainless steel wire so that the composite article exhibits a total outside diameter no greater than the diameter of prior art stainless steel orthodontic arch wires. The article of manufacture exhibits properties of flexibility and resiliency significantly greater than that of the prior art stainless steel wires. It is also found that the steel reinforced plastic rod posseses characteristics superior to Nitinol arch wire as far as its resistance to deformation is concerned. It is also less brittle and does not break as readily as Nitinol wire. The article can be easily shaped while remaining effective for its intended purpose.

While the plastic is generally clear, if desired, it may be impregnated with suitable colorants and the resulting article can thereby be rendered tooth-colored so as to make it less obtrusive, but this is only a secondary advantage, the primary one being its improved flexibility and high mechanical memory property.

The dental arch wire of the present invention may conveniently be produced in a co-extrusion process wherein the wire is drawn through the extruder during the polysulfone or Ultem plastic extrusion process. The stainless wire is found to adhere well to the plastic and will accommodate bending. Polysulfone and Ultem plastic materials are found not to leech or to absorb water and are stable at body temperatures. They are also highly abrasion resistant and, as such, possess requisite physical properties making them highly suitable as a coating or covering for metallic wires used in orthodontic procedures.

OBJECTS

Accordingly, it is a principal object of the present invention to provide a new and improved article of manufacture useful in the field of orthodontia.

Another object of the invention is to provide an orthodontic arch in which a stainless steel reinforcing strand is placed within a polysulfone or Ultem plastic material.

Another object of the invention is to provide an improved dental arch wire whose total diameter, which is no greater than commonly used stainless steel or Nitinol dental arch wires, but which possesses greater flexibility and increased resiliency.

These and other objects and advantages of the invention will become apparent to those skilled in the art from the following detailed description of a preferred embodiment when considered in conjunction with the accompanying drawings in which like numerals in the several views refer to corresponding parts.

DESCRIPTION OF THE PREFERRED EMBODIMENT

Figure 1:
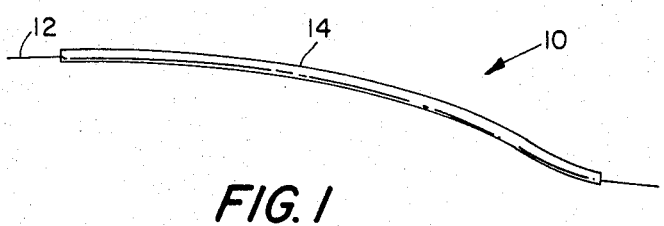
FIG. 1 is a perspective view of the article of manufacture comprising the present invention.
Figure 2:
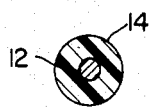
FIG. 2 is a cross-sectional view thereof.
Figure 3:
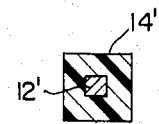
FIG. 3 is a cross-sectional view of an alternative embodiment.

The orthodontic arch wire of the present invention comprises an elongated, wire-reinforced plastic rod which is indicated generally in FIG. 1 by the numeral 10. The central wire 12, which serves as a reinforcing strand, may have a circular cross-section (FIG. 2) or a rectangular cross-section 12' (FIG. 3). The core wire is preferably formed from stainless steel and, in the case of the round configuration, preferably has a diameter in the range of from 0.008 inches to 0.014 inches. With the rectangular cross-section, the dimensions may be in the range of from 0.010 inches×0.016 inches or 0.012 inches×0.018 inches.

As those skilled in the art are aware, stainless steel has long been used in fabricating orthodontic arch wires. To provide the necessary stiffness for applying physiological biasing forces to the teeth, in the past it has been required that such stainless steel wire have a diameter of approximately 0.016–0.022 inches. As is explained in the aforereferenced Andreasen patent, wires of this dimension lack flexibility needed to bend and shape them so as to conform to the orthodontic bands to which the arch wires are intended to connect. This has made it somewhat difficult to fabricate the dental arch in situ. Additionally, this lack of flexibility limits the working range and, therefore, working time of the wire.

As was indicated in the introductory portion of this specification, I have found that, by using polysulfone resin or Ultem ™ polyetherimide resin material, the latter being manufactured and sold by the General Electric Company, and co-extruding same with a stainless steel strand of a lesser diameter so that the resulting product has an outside diameter in the range of from 0.016 inches to 0.022 inches, the resulting stainless steel reinforced plastic rod arch wire product possesses the desired flexibility property allowing it to be easily formed and bent, and an increase in resiliency, which is the property which affords the biasing force on teeth.

Tests conducted by an independent testing laboratory have shown that for arch wires of identical cross-sectional dimensions, my arch wire, for which I have adopted the trademark "Filaflex", is about twenty-seven times more flexible than commercially available stainless steel arch wires and about seven times more flexible than arch wires fabricated from the Nitinol alloy. This test data was obtained by clamping the rectangular cross-section type arch wires to a flat surface with a predetermined length of each extending beyond the edge of that surface. In each case, the wide dimension was positioned vertically and the narrow dimension horzontally. Identical loads were then applied to each sample at a point one inch out from the fulcrum (edge) and the following table shows the load required to yield the indicated deflections for each of the three samples:

|  | Load at Deflection (Pounds) | | | | | |
| --- | --- | --- | --- | --- | --- | --- |
|  | 0.1" | 0.2" | 0.3" | 0.4" | 0.5" | 0.6" |
| Maxillary ™ 18-8 Stainless Steel (.017 × 0.25) | 0.102 | 0.195 | 0.273 | 0.327 | 0.357 | 0.357 |
| Nitinol ™ Ni Ti alloy (.017 × 0.25) | 0.036 | 0.059 | 0.071 | 0.083 | 0.089 | 0.092 |
| Filaflex ™ Polysulfone on ss (.017 × .025) | 0.002 | 0.005 | 0.008 | 0.011 | * | * |

*force caused bending to the point where cantilevered tip slipped off the fixture.

Thus, it has been determined by load testing that the article of manufacture of the present invention wherein the core wire 12 or 12' is reduced in cross-section so as to lie in the above-described range of cross-sections and then the polysulfone or Ultem plastic is co-extruded to be of a thickness so that the composite article has an outside dimension no greater than the cross-section of the prior art Maxillary stainless steel wire and the Nitonol alloy wire alone, the article of the present invention (Filaflex) exhibits about twenty-seven times the flexibility of the prior art solid stainless steel wire and seven times more flexibility than the Nitinol sample while yielding reduced biasing forces on the teeth. This reduction in force is advantageous in orthodontic work where low but steady biasing forces are deemed more efficacious than higher forces which often result in discomfort and tooth deterioration.

The properties of polysulfone and Ultem that make them highly suitable for use in conjunction with dental arch wires are that they have been certified for contact with blood and other body components, meeting U.S.P. XIX, Class VI Requirements; they have a resistance to autoclave sterilization, as well as to other methods; and they comply with F.D.A. regulations for repeated use in contact with food. Polysulfone and Ultem both have a high resistance to acids, alkalis and salt solutions. Also, they are highly stable materials so that environmental variations, such as temperature change or water immersion, result in exceptionally small dimensional changes.

In that colorants may be added to the polysulfone or Ultem polymers prior to their extrusion and orientation without detracting from their physical properties, it is possible to go from a transparent clear color to one that will match the color of teeth, making the resulting dental arch less noticeable than it is when shiny stainless steel is employed.

The inherent hardness of both polysulfone and Ultem allows them to withstand the chewing forces and other orthodontic forces within the mouth. Being abrasion resistant, they are less subject to rupture during installation or thereafter. No other plastics meet these criteria.

It has been found that the Filaflex plastic arch wire of the present invention is not as subject to permanent deformation as is stainless steel and, hence, its ability to impose biasing forces on the teeth after being bent and/or twisted is not impaired. Furthermore, whereas the use of 18-8 stainless steel required a treatment modality in which every few weeks it would become necessary to replace a given arch wire with one of successively increasing cross-sectional size, the use of the arch wire made in accordance with the present invention significantly reduces the frequency with which the arch wires needs replacing. During the initial stages of treatment where the teeth may be badly maloccluded, the flexibility of my arch wire allows it to be bent and formed so as to reach these teeth that deviate most radically from the desired alignment and the memory properties of my wire will exert a low, steady force on the affected tooth (teeth) until it is brought into substantial alignment with neighboring teeth.

While preferred embodiments of the invention have been shown and described, it will be apparent to those skilled in the art that changes can be made in these embodiments without departing from the principles and spirit of the invention, the scope of which is defined in the appended claims. Accordingly, the foregoing embodiments are to be considered illustrative, rather than restrictive of the invention, and those modifications which come within the meaning and range of equivalency of the claims are to be included therein.

What is claimed is:

1. In an orthodontic system for imparting corrective forces to teeth which includes appliances mounted on the teeth and an arch wire connected to said appliances, the improvement being in the arch wire which comprises a plastic body of a cross section fitting and coacting with the appliances to apply forces thereto, and a reinforcing metal core disposed centrally within said body, the cross sectional area of the core being less than one half of the total cross sectional area of said arch wire, whereby the force capability of said arch wire is substantially less than that of a metal arch wire of the same total cross sectional area.

2. The arch wire of claim 1, wherein the metal core is round in cross section.

3. The arch wire of claim 2, wherein the body cross section is round.

4. The arch wire of claim 1, wherein said metal core is stainless steel wire.

5. The arch wire of claim 1, wherein the body cross section is rectangular.

6. The arch wire of claim 1, wherein the body cross section is round.

7. The arch wire of claim 1, wherein the arch wire exhibits a flexibility many times greater than nickel titanium alloy arch wire of the same cross section.

8. The arch wire of claim 1, wherein the plastic body is polyetherimide resin material.

9. The arch wire of claim 1, wherein the plastic body is polysulfone resin material.

10. The arch wire of claim 1, wherein the plastic body is extruded.

* * * * *